United States Patent [19]
Klein et al.

[11] Patent Number: 5,334,157
[45] Date of Patent: Aug. 2, 1994

[54] CATHETER INTRODUCER

[75] Inventors: James K. Klein, Boerne; George E. Sinko, San Antonio, both of Tex.

[73] Assignee: Gesco International, Inc., San Antonio, Tex.

[21] Appl. No.: 118,522

[22] Filed: Sep. 9, 1993

[51] Int. Cl.$^5$ ............................................. A61M 25/01
[52] U.S. Cl. ..................................... 604/160; 604/165
[58] Field of Search ................. 604/177, 160, 161, 165

[56] References Cited

U.S. PATENT DOCUMENTS

| | | | |
|---|---|---|---|
| 3,788,326 | 1/1974 | Jacobs | 604/161 |
| 4,362,156 | 12/1982 | Feller, Jr. et al. | 604/177 |
| 4,445,893 | 5/1984 | Bodicky | 604/177 |
| 4,983,163 | 1/1991 | Mourehead | 604/161 |
| 5,000,745 | 3/1991 | Guest et al. | 604/167 |
| 5,098,392 | 3/1992 | Fleischhacker et al. | 604/161 |
| 5,141,497 | 8/1992 | Erskine | 604/177 |
| 5,221,263 | 6/1993 | Sinko et al. | 604/161 |

Primary Examiner—Paul J. Hirsch
Attorney, Agent, or Firm—Cox & Smith Incorporated

[57] ABSTRACT

A catheter introducer comprises an elongated sheath having a bore to receive a percutaneous needle therethrough. The proximal end of the sheath is secured to a head element having angularly spaced wing portions and defining two opposed parallel planar surfaces. The percutaneous needle has a transversely disposed U-shaped element secured to its proximal end which is snugly engagable with the planer sidewalls of the head portion and is secured thereto through a rib and slot interengagement of the arms with the planar surfaces. The sheath and the entire head portion are provided with diametrically opposed scorelines to permit the ready separation of the introducer through the application of a separating force to the wing portions. Such separation cannot, however, occur so long as the needle is fully inserted within the introducer due to the restraining action of the arms of the U-shaped element.

4 Claims, 4 Drawing Sheets

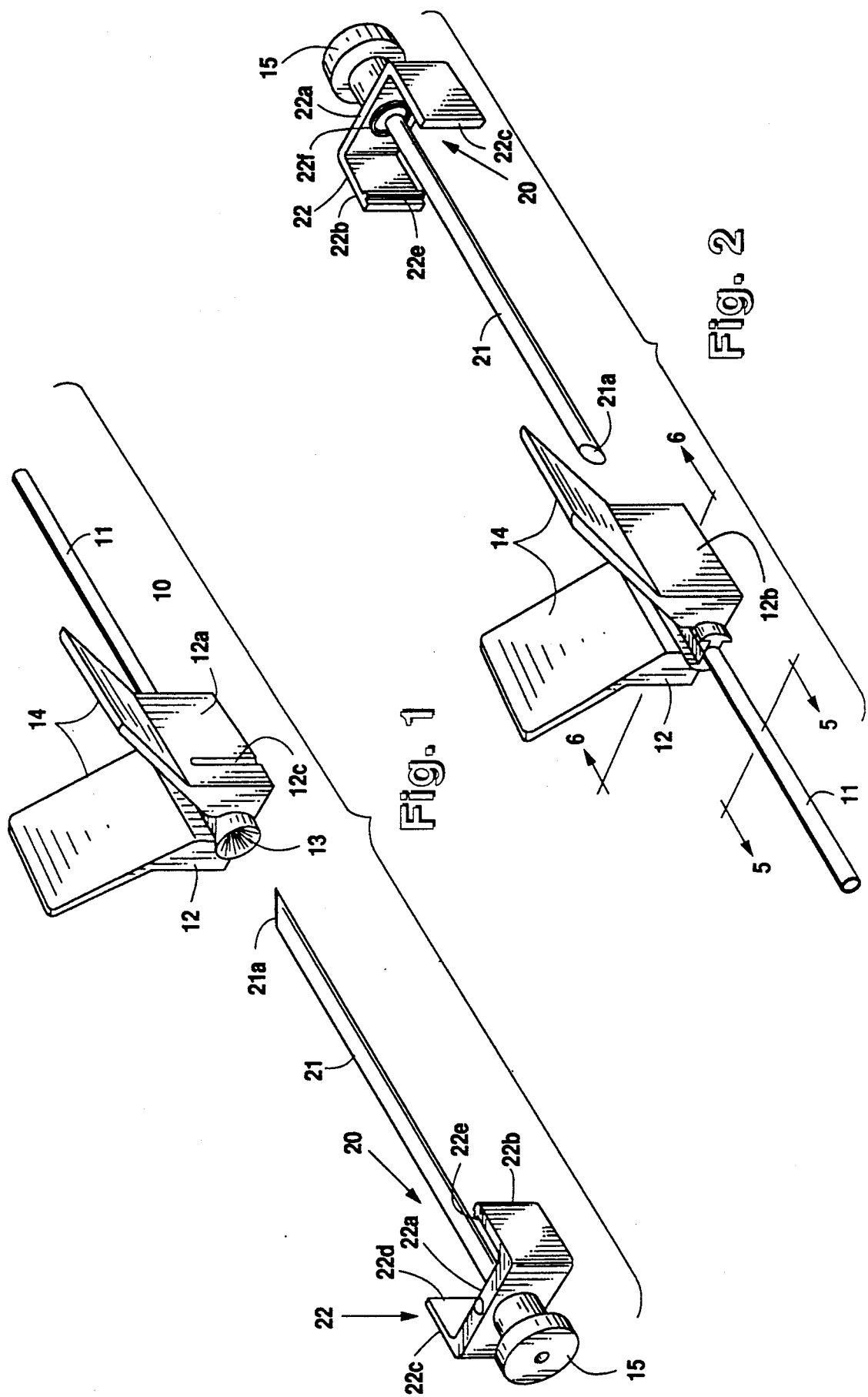

CATHETER INTRODUCER

FIELD OF THE INVENTION

This invention relates to an apparatus for inserting small diameter catheters an extended distance into human veins, and particularly an introducer apparatus that may be axially split for removal from the catheter after the catheter is properly positioned in a selected vein.

BRIEF DESCRIPTION OF THE PRIOR ART

As shown in U.S. Pat. No. 4,306,562 to Osborne, it is desirable to provide a catheter introduction apparatus which will permit the catheter to be moved an extended distance through a vein of the patient to a location adjacent a particular organ. Such insertion must be accomplished without rupturing the vein, other than by the initial piercing of the vein by a percutaneous needle. The catheter introduction device preferably includes an elongated tubular sheath which has a bore permitting the insertion of the needle to an extent that the sharpened end thereof projects out of the distal end of the tubular sheath. Vein penetration is accomplished by the projecting sharpened end of the needle and subsequent relative movement of the tubular sheath over the needle permits the distal end of the sheath to be inserted within the selected vein. The needle may then be withdrawn and the distal end of the catheter inserted through the sheath and into the vein, and then moved the desired distance through the vein to a desired location.

At this point, it is very desirable to effect the removal of the introducer from the body to minimize the possibility of infection or other adverse reaction of the body tissue to the presence of the sheath. A small diameter catheter may, however, remain in place in the vein for an extended period. To remove the catheter guide or sheath, the aforementioned Osborne patent proposes that the sheath be made of longitudinally molecularly oriented material and provide slits in the proximal ends of the sheath which permit the proximal ends to be grasped and a severing force applied to the axial severable material of the sheath. A similar technique has been employed for the insertion of pacemaker electrodes. See U.S. Pat. No. 4,166,469 to Littleford.

Such prior art devices have, however, two disadvantages, particularly whenever a small diameter catheter must be employed, such as would be used in the veins of neonatal patients. It is understood that such small diameter catheters generally have a external diameter of less than 0.1 inches. To introduce this small end of a very flexible element into the equally small bore of the catheter guide or sheath requires a fair amount of manual dexterity on the part of the medical technician to insert the catheter, particularly with blood flowing out the bore of the sheath. Additionally, there is the problem that once the catheter is inserted, the removal of the catheter sheath, through the application of opposing radial forces thereto, very often results in the displacement of the catheter from its desired position in the vein, due to a substantial force being required to effect the axial severance of the entire introducer apparatus.

An effective solution to these two problems has been provided by the construction disclosed and claimed in co-pending application Ser. No. 07/922,315 filed Jul. 30, 1993 and assigned the assignee of the present invention. This allowed application provides a catheter introducer having a sheath rigidly bonded in the bore of an actuating apparatus. Such apparatus includes two diametrically opposed ears for imparting a radial separating or splitting force to the entire apparatus. The sheath and the bore of the actuating apparatus are provided with diametrically opposed, longitudinally extending slots to facilitate the stripping of the apparatus from the inserted catheter. A particular feature of that invention lies in the fact that the slots in the actuating apparatus are actually formed in two diametrically opposed thin conical webs. As a result, a minimal force is required to be applied to diametrically opposed manually graspable ears which are integrally formed on the actuator.

The fact that the axial splitting of the sheath and the actuator portion of the introducer may be accomplished with minimal force does present another problem, in that significant manual manipulation of the introducer must be accomplished during the insertion and withdrawal of the needle, and the subsequent insertion of the sheath into the vein. It occasionally happens that the technician holding the introducer by the ears inadvertently imparts diametrically opposed radial forces to the ears and initiates the splitting of the introducer before the catheter is inserted therein.

There is a need, therefore, for a catheter introducing apparatus which may be readily splitable after the catheter is inserted in a particular vein, but which incorporates a positive resistance to axial splitting of the introducer during the manipulations of the introducer preceding and accompanying the installation of the catheter into the desired vein through the introducer.

SUMMARY OF THE INVENTION

This invention provides a catheter introducer, particularly useful with children or neonatal patients having small veins, comprising an elongated tubular plastic sheath having an external diameter small enough to be readily insertable in a selected vein, and a bore having an internal diameter sufficiently large to permit a desired diameter of catheter to be readily passed through the bore of the sheath. A percutaneous needle is insertable through the proximal end of the bore of the sheath to an extent that the sharpened end of the needle projects out of the distal end of the sheath, so that penetration of the selected vein by the needle permits the distal end of the sheath to be moved forwardly relative to the needle to enter the selected vein. The needle may then be withdrawn from the introducer and a catheter inserted through the bore of the introducer to enter the selected vein and be moved therein to a desired location.

To effect the axial splitting of the introducer after the catheter has been inserted, this invention provides an operating member for the sheath formed from a molded plastic material and having a central hub portion defining a bore which is rigidly bonded to the proximal end of the sheath.

Two radially projecting, manually graspable wing portions are also integrally formed on the operating member and are preferably disposed at an angle of from 70° to 120° relative to each other so as to permit the convenient grasping of such wings by one hand of the technician. Two opposed planar surfaces are provided on the operating member for a purpose to be described.

The sheath is provided with diametrically opposed, longitudinally extending score lines to facilitate the axially splitting of the sheath. The hub portion of the operating member is similarly provided with grooves that are aligned with the score lines in the sheath. Such grooves are preferably disposed in a plane bisecting the angle between the two wing portions. The proximal end of the bore in the sheath terminates in a thin walled funnel which is also diametrically scored in line with the grooves. Such funnel assists in guiding the small catheter into the bore of the sheath.

Thus, the application of radially opposed forces to the wing portions will effect the axial separation of the entire body portion of the operating member and the sheath into two pieces, thus permitting the complete removal of the introducer from the catheter.

To prevent the inadvertent axially splitting of the introducer during the vein piercing by the sharpened end of the percutaneous needle, or during the movement of the distal end of the sheath of the introducer over the sharpened end of the needle and into the selected vein, or during the initial removal movement of the needle from the introducer, this invention contemplates providing the proximal end of the needle with a transversely extending, generally U-shaped latching head member to which the needle is rigidly fastened by any conventional means, such as an appropriate adhesive or by insertion molding.

The transverse head member is in turn provided with appropriate connection elements to engage the planar sidewalls of the hub portion of the introducer at opposed locations, preferably beneath the wing portions. Such interconnecting means may comprise the spaced arms of the U-shaped needle head member which respectively snugly engage the planar sidewalls of the operating member.

One or both of said planar sidewalls has a notch formed therein which is snap engaged by a projection on one of said arms. This engagement insures that the head member and hub portion remain together and that inadvertent splitting of the hub portion is prevented. The needle is also always oriented with its distal open end facing upwardly relative to the two wings.

In any event, so long as the needle is in its fully inserted position in the introducer, the application of splitting forces to the introducer is effectively prohibited. Of course, as soon as the needle is partially withdrawn, this restraint is removed, but at that point the distal end of the sheath is inserted in the selected vein and the introducer may be firmly taped to the body of the patient, thus minimizing the possibility of accidental application of opposed radial forces to the wings of the introducer sufficient to initiate the splitting thereof.

If it is desired to utilize the aforedescribed introducer on patients other than infants, a hollow transparent extension may be provided on the base face of the U-shaped head member with its bore communicating with the needle bore to function as a flashback port to indicate that the needle has pierced the vein.

Further advantages of the invention will be readily apparent to those skilled in the art from the following detailed description, taken in conjunction with the annexed sheets of drawings, on which is shown a preferred embodiment of the invention.

BRIEF DESCRIPTION OF DRAWINGS

FIG. 1 is an exploded perspective view of a catheter introducer and subcutaneous needle embodying this invention, with the view being taken from the right side of the apparatus.

FIG. 2 is a perspective view similar to FIG. 1 but is an exploded perspective view but the view being taken from the left side of the apparatus.

DETAILED DESCRIPTION OF PREFERRED EMBODIMENT

Figure 3:
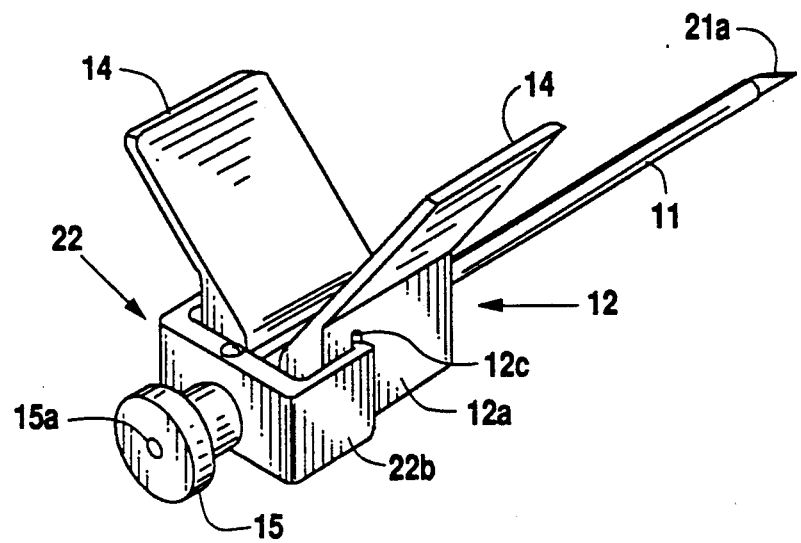
FIG. 3 is a view illustrating the assemblage of the catheter introducer and the subcutaneous needle as viewed from the proximal end of the introducer.

A catheter introducer embodying this invention comprises two elements, namely an introducer 10 and a subcutaneous needle assemblage 20. Introducer 10 comprises a hollow sheath portion 11 having a diameter selected to be insertable within a selected vein of a patient and a bore to receive the needle portion 21 of the needle assemblage 20. On the proximal end of the sheath 11, a hub portion 12 is rigidly secured by adhesive or injection molding of the hub portion around the sheath 11. Hub portion 12 defines two opposed planar surfaces 12a and 12b and each of these surfaces is provided with a vertical groove 12c for a purpose to be hereafter described. A funnel shaped element 13 is also integrally molded on the hub portion 12 and communicates with the proximal end of the bore of the sheath 11.

Figure 5:
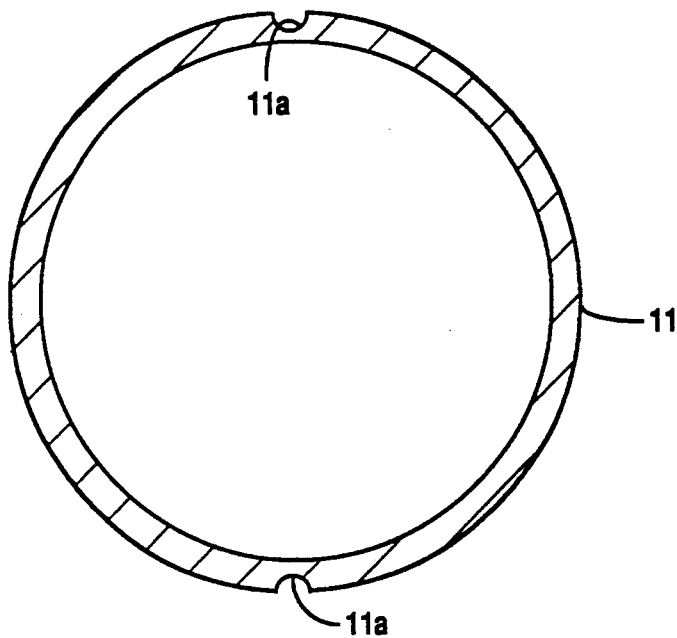
FIG. 5 is a sectional view taken on the plane 5—5 of FIG. 2.
Figure 6:
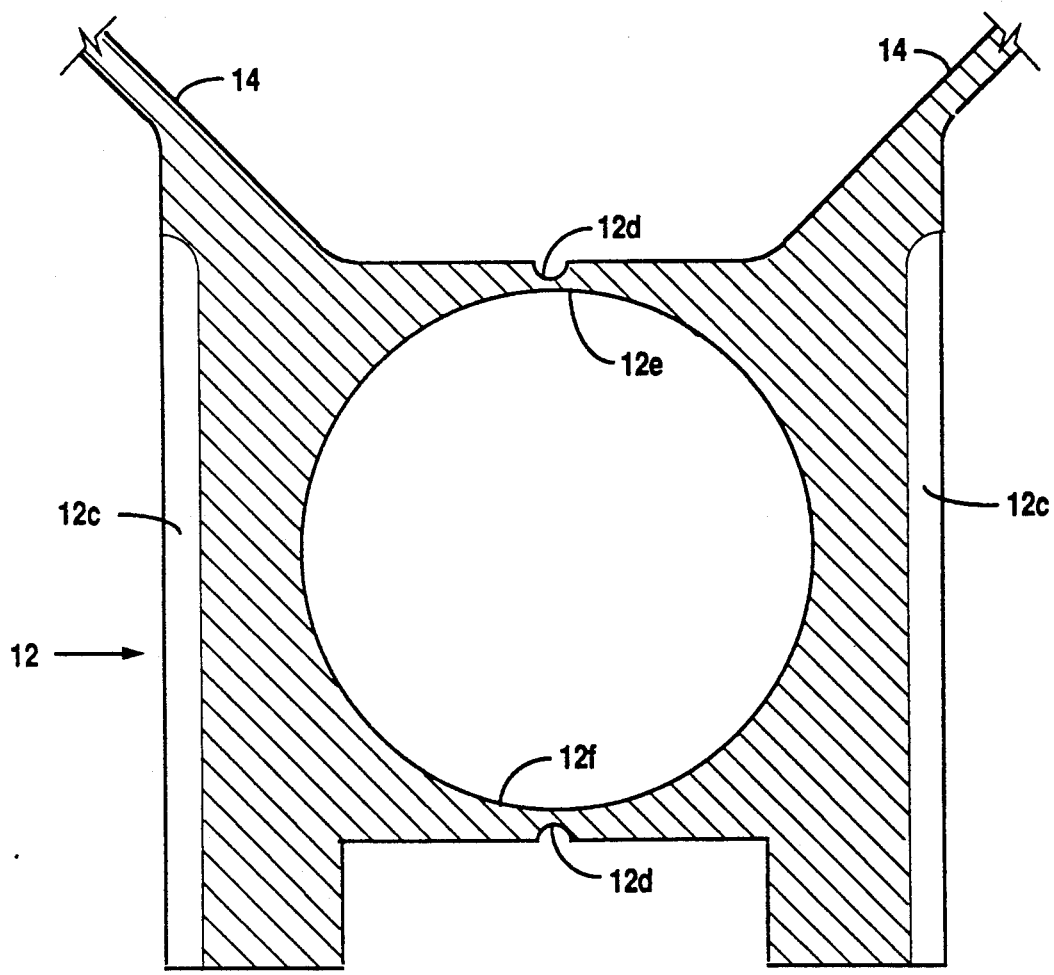
FIG. 6 is a sectional view taken on the plane 6—6 of FIG. 3.
Figure 7:
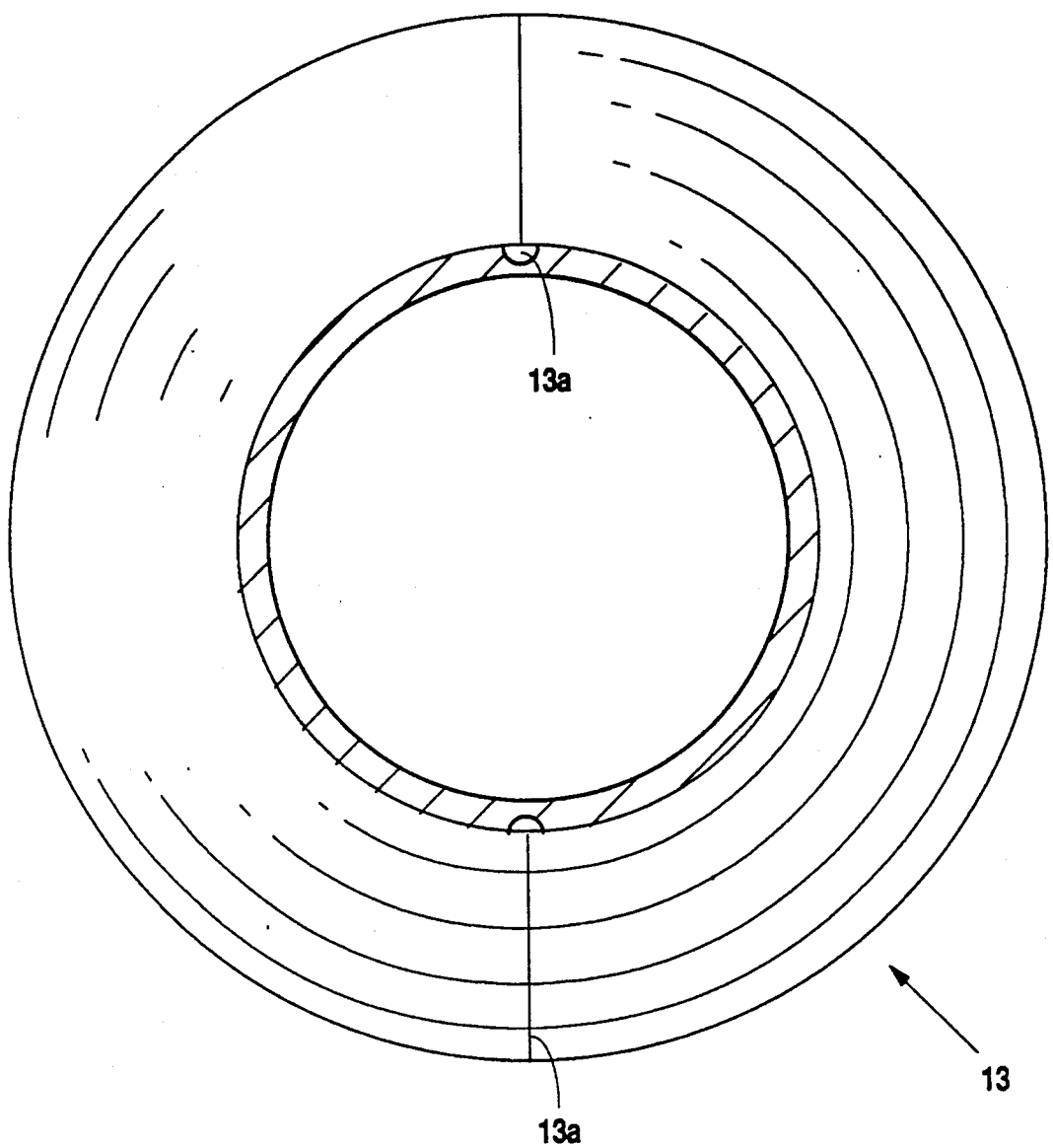
FIG. 7 is a sectional view taken on the plane 7—7 of FIG. 1.

As best shown in FIGS. 5, 6 and 7, diametrically opposed, aligned scorelines 11a and 12d are respectively formed in the sheath 11, hub portion 12, so as to permit the ready axial separation of the introducer 10. Funnel 13 is split in alignment with the scorelines as indicated at 13a. The hub portion 12 has thin walls 12e and 12f along which score lines 12d are formed.

To facilitate the handling of the introducer 10 and to conveniently effect the axial seperation thereof, a pair of angularly disposed wing portions 14 are integrally formed on hub portion 12 and define an included angle ranging from 70° to 120°. The scorelines 11a, 12d and slit 13a preferably lie in a plane bisecting the wing portions 14. Thus the application of a separating force to the wing portions 14 will effect an axial splitting of the hub portion 12, the funnel 13 and the sheath 11.

Figure 4:
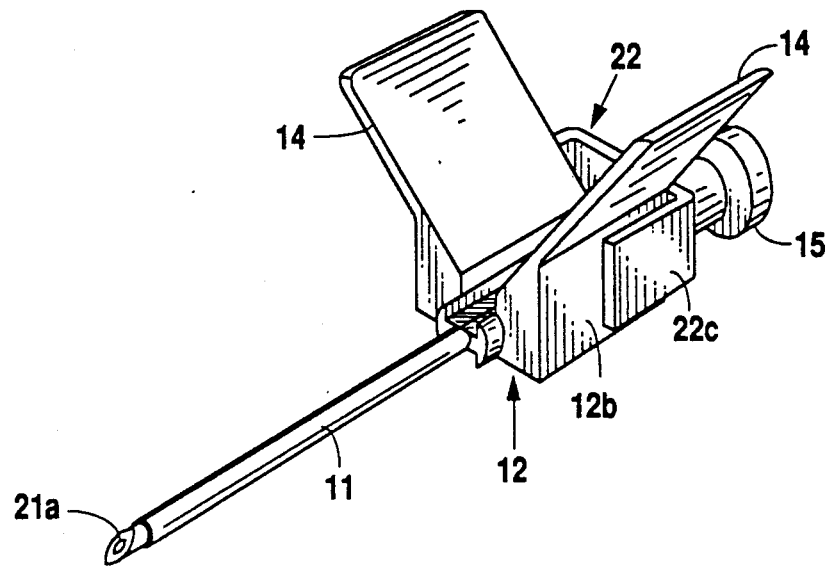
FIG. 4 is a perspective view similar to FIG. 3 but taken from the distal end of the introducer.

The needle element 21 has the customary sharpened end portion 21a. The other end portion is rigidly secured within a transversely disposed latching head member 22. Latching head member 22 has a base portion 22a secured to the proximal end portion of percutaneous needle 21, and two parallel arm portions 22b and 22c which are spaced apart so as to snugly engage the planar surfaces 12a and 12b provided on the hub portion 12 of the introducer element 10. One arm portion 22b defines an inwardly projecting ridge 22e which is engagable with a vertical slot 12c provided in one of the planar surfaces 12a and 12b of hub portion 12. Thus, when the needle 21 of the needle assemblage 20 is fully inserted through the hub portion 12 and sheath 11 so that the distal sharpened end 21a of the needle projects outwardly from such sheath portion as shown in FIGS. 3 and 4, the arms 22b and 22c snugly engage the planar surfaces 12a and 12b of the hub portion 12 and the ridge 22e snaps into engagement with the vertical slot 12c, thus effecting the securement of the elements together for the vein puncturing step, and during the insertion of the distal end of the sheath 11 into the punctured vein. The engagement of ridge 22e with slot 12c insures that the open end 21a of needle 21 is facing upwardly relative to wings 14. In this position, an annular ridge 22f on base portion 22a surrounding the needle element 21 sealingly engages the inner wall of funnel element 13. To facilitate the handling of introducer 10, a knob 15 having a bore 15a is rigidly secured to or integrally molded to the proximal end of base portion 22a.

The needle element 21 is then withdrawn from the hub portion 12 and discarded. A small catheter (not shown) is then inserted through the funnel shaped portion 13 of hub portion 12 and fed through the sheath 11 and into a vein. Obviously, such catheter may be moved to any desired position within the selected vein.

A separating force is then applied to the wing elements 14 causing the introducer 10 to axially split into two components and thus be removed from the catheter. Due to the angular position of wings 14, the initial separation can be accomplished by spreading the fingers of one hand.

The utilization of a locking head 22 on the proximal end of the needle prevents the axial splitting of the hub portion 12 when engaged with the opposed planar surfaces 12a and 12b. Thus premature inadvertent splitting of the hub portion 12 and the connected sheath 11 is minimized.

Figure 8:
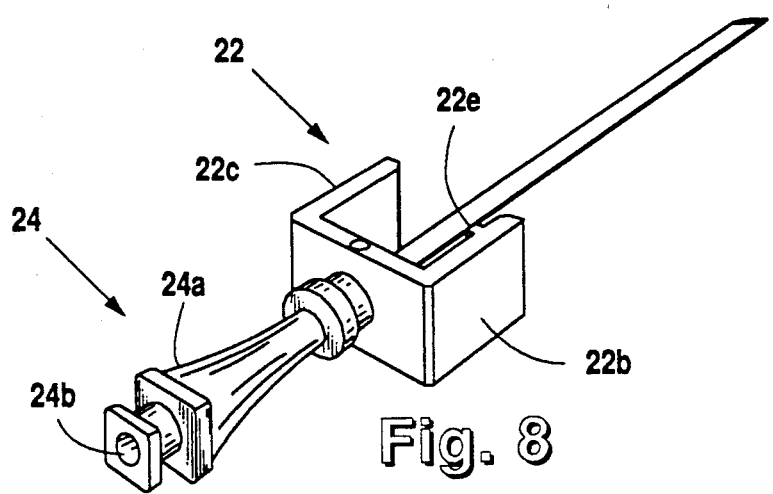
FIG. 8 is a view of the needle head element with a flash element added.

A modification of this invention is illustrated in FIG. 8 which is particularly desirable when the introducer 10 is utilized with larger children and adults. For such applications, it is desirable to provide a so called flash indicator which provides a visible show of blood when the sharpened end of the needle element 21 pierces the vein. Such flash element may comprise a hollow transparent extension 24 of the latching member 22. Extension 24 is provided with an enlarged chamber 24a which in turn communicates with a smaller diameter bore 24b opening to the atmosphere to permit air displaced by the surge of blood to be exhausted from the chamber 24a.

Modifications of this invention will be readily apparent to those skilled in the art, and it is intended that all such modifications be included within the scope of the appended claims.

What is claimed and desired to be secured by Letters Patent, is:

1. A catheter introducer comprising, in combination:
a tubular plastic sheath having an external diameter small enough so that the distal end thereof may be readily insertable in a selected human vein and an internal bore diameter sufficiently large to permit a desired diameter of catheter to enter the proximal end and to be readily passed through the bore of said sheath;
a percutaneous needle having a sharpened open distal end insertable through said bore of said sheath to an extent that the sharpened open end of said needle projects out of the distal end of said sheath, whereby penetration of a selected vein by said needle permits the distal end of said sheath to be moved forwardly relative to said needle to enter the selected vein;
said sheath having a pair of diametrically opposed, longitudinally extending score lines, whereby the application of opposed radial forces to the proximal end of said sheath at locations respectively intermediate said score lines will produce a longitudinal splitting of said tubular sheath;
an operating member for said sheath formed from molded plastic material;
said operating member comprising a central hub portion having a bore rigidly bonded to the proximal end of said sheath;
said central hub portion having longitudinal slots respectively disposed in alignment with said score lines in said sheath;
a pair of manually graspable, radially projecting wings respectively secured to said hub portion intermediate said slots, whereby opposed forces applied to said wings effect the longitudinal splitting of said hub portion and said sheath,
a pair of opposed parallel planar surfaces respectively formed on said operating member;
a generally U-shaped head secured to the proximal end of said needle;
said head having a bight portion and spaced arm portions respectively snugly engagable with said planar surfaces when said bight portion abuts said hub portion, thereby resisting forces on said wings tending to longitudinally split said hub portion;
a notch formed in only one of said planar surfaces; and
a projection formed on only one of said arms snap-engagable with said notch, thereby securing said needle head to said operating member and orienting said needle opening relative to said wings.

2. The apparatus of claim 1 further comprising a funnel formed on the proximal end of said hub portion to assist insertion of a catheter into the bore of said sheath after removal of said needle.

3. The apparatus of claim 2 further comprising an annular ridge on said bight portion of said U-shaped needle head sealingly engaging said funnel when said needle head abuts said hub portion.

4. The apparatus of claim 1 further comprising a hollow transparent extension formed on said head portion and defining a flash chamber for blood flowing through said needle to indicate vein penetration.

* * * * *